United States Patent [19]

Knoll

[11] 4,175,560

[45] Nov. 27, 1979

[54] SWAB

[75] Inventor: Ernst Knoll, Herrengassle 3, 7801 Umkirch bei Freiburg, Fed. Rep. of Germany

[73] Assignees: Paul Hartmann AG; Ernst Knoll; Werner Thieme, all of Fed. Rep. of Germany

[21] Appl. No.: 812,435

[22] Filed: Jul. 1, 1977

Related U.S. Application Data

[63] Continuation of Ser. No. 743,930, Nov. 22, 1976, abandoned.

[30] Foreign Application Priority Data

Nov. 21, 1975 [DE]  Fed. Rep. of Germany ....... 2552172

[51] Int. Cl.² ............................................. A61M 35/00
[52] U.S. Cl. .................................... 128/269; 128/270; 128/285
[58] Field of Search ............. 128/269, 260, 2 W, 270, 128/285, 263; 15/209 R; 19/144; 28/118

[56]  References Cited

U.S. PATENT DOCUMENTS

| | | | |
|---|---|---|---|
| 2,264,586 | 12/1941 | Ross | 128/270 X |
| 2,710,007 | 6/1955 | Greiner et al. | 128/285 X |
| 3,359,981 | 12/1967 | Hochstrasser | 128/285 |
| 3,542,025 | 11/1970 | Gustafson | 128/269 |
| 3,976,075 | 8/1976 | Chinai et al. | 128/285 |

FOREIGN PATENT DOCUMENTS 466048 of 1928 Fed. Rep. of Germany ........... 128/270

Primary Examiner—Stephen C. Pellegrino
Attorney, Agent, or Firm—Craig and Antonelli

[57]   ABSTRACT

A swab of absorbent material, especially for medicinal purposes, which is in the form of a strip which is wound so as to form a plurality of layers with at least the outer edges of the outermost layer of the wound strip being thrust into the center thereof. The lateral edges are folded so as to form an annular pad consisting of a plurality of layers of the material at the respective ends of the swab. To provide for a double layer swab, the strip of material is folded about an axis extending transversely to the longitudinal direction of the strip of material so as to bring the two ends of the strip into substantial alignment with the strip then being wound from the substantially aligned ends toward the fold so that the fold is disposed on the outermost surface of the swab.

13 Claims, 6 Drawing Figures

SWAB

This application is a continuation of U.S. patent application Ser. No. 743,930, filed Nov. 22, 1976, now abandoned.

The present invention relates to a cleaning pad and, more particularly, to a swab fashioned of an absorbent textile material and employed for medicinal purposes.

Swabs for medicinal purposes in the treatment of wounds and/or in surgery have been proposed which have an irregular ovoid form and various lengths and diameters. Generally, the smallest swabs have a length of about one centimeter and a maximum diameter of six to seven millimeters; however, larger swabs have also been proposed.

The proposed swabs have been fashioned from an approximately square piece of muslin which is manually folded to form a triangle with the two outer points of the triangle then being manually knotted and the remaining muslin ends being manually thrust as firmly as possible into the knot. In the manufacture of swabs, it is essential that the swab be tucked together as tightly and firmly as possible so, when used to absorb fluid, the swab will not loosen and possibly give off free ends of thread, thereby contaminating the wound.

One disadvantage of the afore-mentioned manner of manufacturing swabs resides in the fact that the individual swabs can only be produced with great manual dexterity.

A further disadvantage of the proposed swabs resides in the fact that, due to the presence of knots in the center of the swabs, an undesirable hardening and thickening of the swab results which can adversely affect the exact handling of the respective swabs by pincers or the like.

Yet another disadvantage of the proposed swabs resides in the fact that the maximum density of the swab is located at the center thereof so that a swab can only be grasped with pincers with some difficulty and the frontal faces of the swab, which are loosely packed, cannot always be employed for a wiping of the edges of the wounds or the like. Moreover, because of the inhomogeneities which are present in the proposed swabs, the absorptive capability of such swabs varies over the periphery thereof.

In German Pat. No. 562,059, a cleaning pad or swab is described wherein a pad insert is wound to a roll from a strip of cellulose which is placed in a knitted tubular casing which extends somewhat over the front faces of the roll. The extending ends of the casing are turned in or inserted from both sides into the middle opening of the roll. By virtue of this arrangement, the front faces of the roll insert are well covered and the outer part of the middle roll opening is secured and closed with the ends of the tubular casing being securely fastened within the roll insert.

In United Kingdom Pat. No. 508,610, a pad is disclosed wherein absorbent material such as cotton wool and a piece of knitted open mesh fabric having a length which is slightly more than twice the length of the pad is provided. The pad is wrapped around the fabric and an exposed length of the fabric is then doubled back over the pad and tucked into a tubular hollow form in the pad.

One disadvantage of each of the last-mentioned pads resides in the fact that a separate tubular casing or mesh fabric is necessary to encapsulate the absorbent material forming the pad.

A further disadvantage of the last-mentioned pads resides in the fact that, by virtue of the provision of the hollow tubular central core in the production of the respective pads, a uniform absorption is not always ensured.

The aim underlying the present invention essentially resides in providing a swab, the manufacture of which is greatly facilitated and which minimizes, if not avoids, any inhomogeneities adversely affecting the absorptive capability of the swab.

According to one feature of the present invention, a length of textile material is cut into a strip and tightly wound into a plurality of layers with at least the outer edges of the outermost layer of the strip being thrust or tucked into the center of the wound strip. By virtue of this arrangement, it is possible to prepare a swab in a simple way since the rolling up of the strip of textile material presents no special requirements with respect to manual dexterity. Moreover, the tucking in or thrusting of the outer edges of the strip of material into the interior can be effected relatively simply and a swab results which has no localized thickened portions which result from a knotting or the like of the material.

Additionally, since the outer edges of the strip material forming the swab are covered over by the outermost layer of material which forms an outer sheath, it is not possible for free thread ends to become loose during a use of the swab.

According to another advantageous feature of the present invention, the strip of textile material is wound into a cylindrical form and all outer edges of the individual layers of the strip of material are then thrust or tucked into the center of the rolled strip. Preferably, the outer zones thrust into the center are folded over so that the individual layers in the outer zone lie essentially parallel on each other in such a way that the outermost layer is entirely at the inside and all other layers are disposed essentially as strata toward the outside to the innermost layer of the wound strip. By this arrangement, the folded over outer zones form an annular pad built up by a multiplicity of layers and a thickening of the swab is realized in the end zones thereof without providing localized thickened portions or inhomogeneous places.

According to yet another feature of the present invention, the strip of material is folded together about a central area extending transversely to the longitudinal direction of the strip so as to form a double layer. The strip is subsequently rolled from the free ends of the strip toward the fold resulting in the fold forming the end of the outermost layer of the rolled-up strip. By virtue of this feature, even the outermost layer of the swab is not provided with free edges of the material from which free thread ends or lint could work loose, thereby causing the risk of a substantial infection during a surgical operation which is to be avoided at all costs.

One advantage of the swab of the present invention resides in the fact that it can be handled especially well and can receive a particularly taut and firm form by virtue of the thicker layering at the frontal faces of the swab. Specifically, when the swab is in use, it is normally grasped by pincers in the center thereof so that the particularly firm and strongly constructed end zones can be utilized very well for wiping out wound edges or for separation of flesh from bone.

A further advantage of the present invention resides in the fact that a swab is produced which has, as compared to manually produced swabs, a substantially greater bulk of material in the end zones which are fashioned as annular pads so that the absorbing properties and take-up capabilities for secretions and blood are also improved due to a better utilization of the materials.

According to a further advantage of the present invention, by controlling the tension that is exerted on the strip of material during a winding process of the swab, it is relatively simple to determine the final density of the finished swab.

Accordingly, it is an object of the present invention to provide a swab which avoids by simple means the afore-mentioned shortcomings and disadvantages encountered in the prior art.

A further object of the present invention resides in providing a swab which is substantially better for wound treatment especially for wiping out wound edges or the like.

Yet another object of the present invention resides in providing a swab which can be made substantially more easily and without great manual dexterity.

A further object of the present invention resides in providing a swab that has a homogeneous composition and uniform density over its periphery.

These and other objects, features and advantages of the present invention will become more apparent from the following description when taken in connection with the accompanying drawings which show, for the purposes of illustration only, one embodiment in accordance with the present invention, and wherein.

Figure 1:
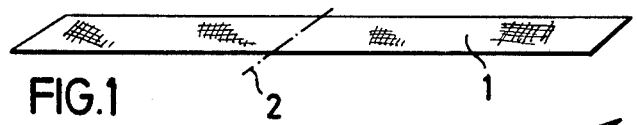
FIG. 1 is a perspective view of a textile strip employed in the manufacture of a swab in accordance with the present invention.

Referring now to the drawings wherein like reference numerals are used throughout the various views to designate like parts and, more particularly, to FIG. 1, according to this figure, a strip 1 of material of a specific length is provided having a center area 2 and two ends or edges 3. The strip 1 may be made of, for example, woven or unwoven textile flat structures of natural or synthetic fiber, e.g., muslin or also of a web material.

Figure 2:
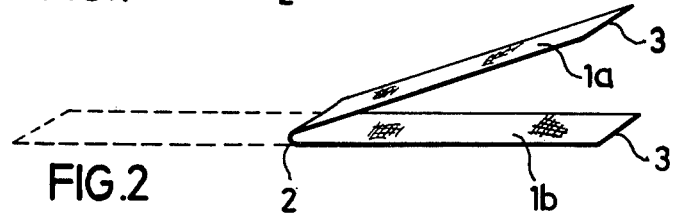
FIG. 2 is a perspective view of a folding of the strip of FIG. 1.
Figure 3:
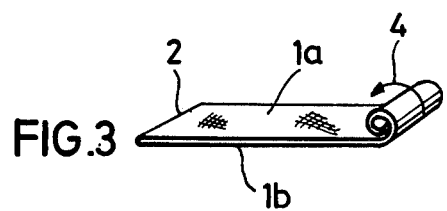
FIG. 3 is a perspective view of the beginning of the winding of the folded strip of FIG. 2.
Figure 4:
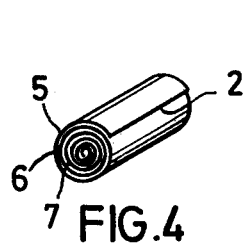
FIG. 4 is a perspective view of the completely wound strip of FIGS. 1-3.

As shown in FIGS. 2-4, the strip 1 of material is first folded along the center area 2 so as to define an upper and lower layer 1a, 1b. Preferably, the ends of edges 3 are aligned as exactly as possible and the strip 1 is then wound in the direction of arrow 4 from the aligned ends or edges 3 toward the center area 2 so as to result in the formation of a cylindrical roll having a plurality of layers 5, 6, 7 of material of strip 1.

Figure 5:
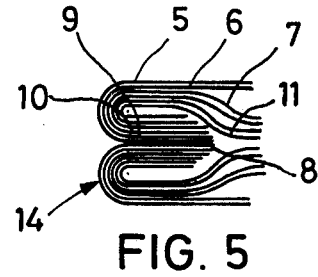
FIG. 5 is a partial longitudinal sectional view through a finished swab according to the present invention.

As shown in FIG. 5, edge zones 8, 9, 10 of the respective layers, 5, 6, 7 are then thrust or tucked inwardly into the center of the formed cylindrical roll so that the outermost layer 5 with its edge zone 8 is disposed substantially centrally of the formed cylindrical roll and the edge zones 9, 10 of the layers 6, 7 adjacent thereto are layered on each other from inside the formed cylindrical roll toward the outside thereof. Layers 5, 6, 7 run substantially parallel to each other until they adjoin an innermost layer 11 of the formed cylinder of the strip 1 of material.

Figure 6:
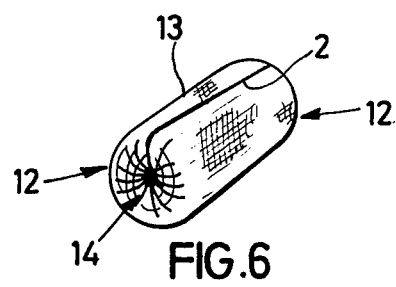
FIG. 6 is a perspective view of a completed swab according to the present invention.

As shown in FIG. 6, the thrusting or tucking of the edge zones 8, 9, 10 into the formed cylinder results in a densification or thickening of material in the edge zones generally designated by the reference numeral 12 of a finished swab 13, which densification or thickening remains homogeneous over the entire periphery of the swab 13. Additionally, on the end faces of the swab 13, annular pads generally designated by the reference numeral 14 are formed which are particularly stable in construction, thereby rendering the swab 13 especially suitable for treating surgical wounds.

It is also possible in accordance with the present invention to fold only the outermost layer 5 in the outer zone into the center of the formed cylinder so that no free threads are provided at the respective ends of the finished swab 13.

If no thickening or densification is desired in the edge zones 12, the strip 1 of starting material may be fashioned so as to decrease in width in the region of the outermost layers. Thus, for example, a predetermined length of the strip of material in the center area 2 may have a first width with such width becoming narrower from the central area 2 toward the respective ends or edges 3. Upon a folding and rolling of such strip in the manner illustrated in FIGS. 2-4, it would then be sufficient to thrust or tuck inward the wider zone of the outermost layers that project beyond the inner zone and, as a result thereof, there would be no thickening or densification in the zones 12.

It is also possible in accordance with the present invention to avoid densification or thickening in the edge zones 12 by having the respective edge zones 8, 9, 10 thrust or tucked in somewhat into the middle of the cylindrical form of the swab so that no thickening of material would occur over the length of the swab.

In addition to the above-noted advantages of the swab 13 of the present invention, the arrangement illustrated in FIG. 5 facilitates the handling of the swab particularly for the treatment of wounds by virtue of the annular pads providing compact and stable edges.

While I have shown and described only one embodiment in accordance with the present invention, it is understood that the same is not limited thereto, but is susceptible of numerous changes and modifications as known to those skilled in the art, and I therefor do not wish to be limited to the details shown and described herein, but intend to cover all such changes and modifications as are encompassed by the scope of the appended claims.

I claim:

1. A swab comprising: a strip of material having two spaced ends interconnected by spaced lateral edges, said strip of material being wound about an axis extending transversely to a longitudinal direction of the material so as to form a plurality of individual layers disposed one above the other with one of said individual layers defining an outermost surface of the swab, and wherein each lateral edge of each of said individual layers of the swab is tucked into a center of the wound strip of material.

2. A swab according to claim 1, wherein a fold extending transversely of a longitudinal direction of the strip of material is provided so as to bring said two ends into substantial alignment and form a double layer of material.

3. A swab comprising: a strip of material having two spaced ends interconnected by spaced lateral edges, said strip of material being wound about an axis extending transversely to a longitudinal direction of the material so as to form a cylindrically shaped swab having a plurality of individual layers disposed one above the other with one of said individual layers defining an outermost edge of the swab, and wherein each lateral edge of each of said individual layers is tucked into a center of the wound strip of material.

4. A swab according to claim 3, wherein the lateral edges thrust into the center of the wound strip of material extend essentially parallel to each other, and wherein the lateral edges of the layer defining the outermost surface of the swab are arranged substantially along a longitudinal center axis of the swab.

5. A swab according to claim 4, wherein the lateral edges of the individual layers are folded so as to form an annular pad on respective ends of the swab.

6. A swab according to claim 5, wherein a fold extending transversely of a longitudinal direction of the strip of material is provided so as to bring said two ends into substantial alignment and form a double layer of material.

7. A swab comprising: a strip of material having two spaced ends interconnected by spaced lateral edges, the lateral edges of the individual layers being folded so as to form an annular pad on respective ends of the swab, a fold extending transversely of a longitudinal direction of the strip of material so as to bring said two spaced ends into substantial alignment and form a double layer of material, said strip of material being wound about an axis extending transversely to the longitudinal direction of the material from the substantially aligned two ends toward said fold so as to form a cylindrically shaped swab having a plurality of individual layers disposed one above the other with one of said individual layers defining an outermost surface of the swab and with said fold disposed on the outermost surface of the swab, each lateral edge of each of said individual layers of the swab is tucked into a center of the wound strip of material with the lateral edges thrust into the center of the wound strip of material extending essentially parallel to each other, and wherein the lateral edges of the layer defining the outermost surface of the swab are arranged substantially along a longitudinal center axis of the swab.

8. A swab comprising: a strip of material having two spaced ends interconnected by spaced lateral edges, a fold extending transversely of a longitudinal direction of the strip of material so as to bring said two spaced ends into substantial alignment and form a double layer of material, said strip of material being wound about an axis extending transversely to the longitudinal direction of the material from the substantially aligned two ends toward said fold so as to form a plurality of individual layers disposed one above the other with one of said individual layers defining an outermost surface of the swab and with said fold disposed on the outermost surface of the swab, and wherein at least lateral edges of the layer defining the outermost surface of the swab are tucked into a center of the wound strip of material.

9. A swab comprising: a strip of material having two spaced ends interconnected by spaced lateral edges, said strip of material including a central area between said two spaced ends, said central area having a width which is greater than a width of the strip of material at said two ends, a fold extending transversely to a longitudinal direction of the strip of material so as to bring said two spaced ends into substantial alignment and form a double layer of material, said strip of material being wound about an axis extending transversely to the longitudinal direction of the material from the substantially aligned two ends toward said fold so as to form a plurality of individual layers disposed one above the other with one of said individual layers defining an outermost surface of the swab and with said fold being disposed on the outermost surface of the swab, and wherein at least lateral edges of the layer defining the outermost surface of the swab are tucked into a center of the wound strip of material.

10. A method of producing a swab, the method comprising the steps of:
   providing a strip of absorbent material,
   arranging said strip of material into a plurality of individual layers disposed one above the other about an axis extending transversely to a longitudinal direction of the material, and
   thrusting each lateral edge of each of the individual layers of the swab into a center of the arranged strip of material.

11. The method of claim 10, wherein the step of arranging includes:
   folding the strip of material about an axis extending transversely to a longitudinal direction of the strip of material so as to bring two ends of the material into substantial alignment, and
   winding the folded strip of material from the substantially aligned ends thereof toward the fold.

12. A method of producing a swab, the method comprising the steps of:
   providing a strip of absorbent material,
   arranging said strip of material into a plurality of individual layers disposed one above the other about an axis extending transversely to the longitudinal direction of the material by folding the strip of material about an axis extending transversely to a longitudinal direction of the strip of material so as to bring two ends of the material into substantial alignment, and winding the folded strip of material from the substantially aligned ends thereof toward the fold, and
   thrusting all of the lateral edges of the plurality of individual layers of the swab into a center of the arranged strip of material by folding the lateral edges of the individual layers so that the lateral edge of the outermost layer of the swab is disposed substantially centrally of the swab and the remaining layers are disposed essentially parallel to each other and strata-like toward the outside of the swab up to an innermost layer thereof.

13. The method of claim 12, wherein the step of folding the lateral edges of the individual layers includes:
   forming annular pads of absorbent material at respective ends of the swab.

* * * * *